United States Patent [19]

Sieber

[11] 4,214,790

[45] Jul. 29, 1980

[54] ORTHOPEDIC RECLINING CHAIR

[76] Inventor: Walter P. Sieber, 5 Centre St., Elmira, Ontario, Canada, N3B 2T6

[21] Appl. No.: 6,455

[22] Filed: Jan. 25, 1979

[51] Int. Cl.² .......................... A47C 1/02; A61F 5/00; A61H 1/02

[52] U.S. Cl. .......................... 297/326; 128/70; 272/144; 297/68; 297/468

[58] Field of Search .................. 297/325, 326, 68, 330, 297/465, 468, 466; 5/81 C, 81 R; 128/70, 71, 133, 134, 24 R, 68; 272/134, 144, 145

[56] References Cited

U.S. PATENT DOCUMENTS

| | | | |
|---|---|---|---|
| 2,104,830 | 1/1938 | Collard | 297/468 X |
| 3,060,925 | 10/1962 | Honsaker | 128/70 |
| 3,081,085 | 3/1963 | DeGirolamo | 128/70 |
| 3,173,720 | 3/1965 | Noda | 297/330 X |
| 3,293,667 | 12/1966 | Ohrberg | 128/24 R |
| 3,388,700 | 6/1968 | Mountz | 128/71 X |
| 3,606,453 | 9/1971 | Cicero | 297/468 X |
| 3,752,153 | 8/1973 | Copeland | 128/24 R |
| 3,858,873 | 1/1975 | Jones | 272/134 X |
| 4,145,082 | 3/1979 | Daly | 128/134 |

FOREIGN PATENT DOCUMENTS

| | | | |
|---|---|---|---|
| 7605961 | 12/1976 | Netherlands | 128/70 |

*Primary Examiner*—James T. McCall
*Attorney, Agent, or Firm*—Ridout & Maybee

[57] ABSTRACT

An orthopedic reclining chair is reclinable to a position in which the body of the occupant is substantially inverted, the occupant being retained in the chair by means of a lap belt engaging the upper surface of the thighs whereby to support the weight of the head and torso through the hip joints so as to apply traction to the spine of the occupant. Preferably the heating unit comprises an integral backrest and seat, together with a support for the lower portions of the legs, the seating unit being rockably suspended from a frame relative to which it may be pulled rearwardly from an equilibrium semi-reclining position to its substantially inverted position.

7 Claims, 5 Drawing Figures

ORTHOPEDIC RECLINING CHAIR

FIELD OF THE INVENTION

This invention relates to reclining chairs, and more particularly to a reclining chair which can also be utilized to apply orthopedic treatment to a user.

BACKGROUND TO THE INVENTION AND PRIOR ART STATEMENT

Over the years, a very wide range of reclining chairs have been proposed or actually utilized. These generally fall into two classes, those in which a seat and back rest move as a unit from an upright to one or more reclining positions, and those in which a seat and back rest move to one or more reclining positions accompanied by a change in angle between the back rest and the seat. Such chairs are commonly provided with a fixed or movable leg rest, and may be operated either automatically by body movements of the user or manually, as by means of an operating lever. Commonly, such chairs are capable of assuming a semi-reclining or "T.V." position suitable for reading or watching television, and a more fully reclining position suitable for resting. Many chairs also have provision for locking of the chair, at least in its semi-reclining position. The object of all of these chairs is to promote relaxation of the user.

Such chairs are so well known that it is not in general believed necessary to consider specific examples of such chairs. I would however refer to U.S. Pat. No. 3,235,304 issued Feb. 15, 1966 to H. P. Glass, which provides a convenient illustration of how known reclining chairs differ from the chair of my invention. The chair shown by Glass has a rigid body supporting unit adapted to support the head, back, sides and lower legs of an occupant, this body supporting unit being suspended from a supporting frame, which frame carries a manually operated winding mechanism whereby the chair may be moved between different reclining positions ranging from semi- to fully reclining. However, in common with all other reclining chairs of which I am aware, the chair is not capable of being moved to a position in which the body is to a substantial degree inverted, and if it were so moved, the angles of the head rest and leg rest are such as would respectively tend to support the shoulders of the user and tip the user's legs out of contact with the chair. Moreover, no restraint is provided such as would retain the user in the chair in such a position, let alone the specific type of restraint required by the present invention, a primary object of which is to provide a chair which can be utilized to apply spinal traction to the occupant. The Glass chair, in common with other conventional reclining chairs, is in no way adapted or intended for this purpose.

Spinal traction may be applied by various known methods, but commonly by use of a chiropractor's couch. A patient on such a couch is commonly restrained by the ankles or thorax, and the couch is then tilted to a sufficient angle for the desired degree of traction to be applied to the patient by the action of gravity. A difficulty with the use of leg restraint arises from the fact that the human frame, and in particular the length of the legs, is quite commonly asymmetrical and unless great care is utilized in applying the restraints, it is difficult for the tractive force to be divided evenly between the two legs of the patient. This problem means that such traction can only be administered with skilled assistance, and home treatment, whether with or without such assistance, is usually inpracticable.

The object of the present invention is to provide a device which can be used to apply spinal traction, whilst avoiding the above problems, and which at the same time can also do duty as a conventional reclining chair, and can form an acceptable article of home furnishing.

SUMMARY OF THE INVENTION

An orthopedic reclining chair in accordance with the invention comprises a seating unit comprising a back rest portion and a seat portion maintained at a substantial angle to the back rest, a frame supporting said seating unit for movement between a substantially upright position, and a position in which the body of the user is substantially inverted with the torso inclined at at least 135° to the vertical, reclining mechanism for moving the chair between said positions, and a lap belt operative when fastened to engage the upper surface of the thighs of the user so as to hold the latter substantially parallel to the seat portion of the seating unit.

When the chair is reclined to its substantially inverted position, a major component of the weight of the user's head and torso will be supported by the action of the lap belt on the thighs, and the user's spine will therefore be subject to traction. Because of the angle between the seat and back rest portions of the seating unit, and the action of the lap belt, the weight of the head and torso will be supported substantially equally through the two thigh joints, thus overcoming any difficulties due to differing leg lengths or ineptly applied ankle or leg restraints. Moreover, the lap belt can readily be fastened by the user when the chair is in its upright position. When the chair is upright or tilted to more normal reclining positions it will serve as a conventional reclining chair; it is well known that the use of reclining chairs can afford considerable relief to many sufferers from back problems.

In a preferred arrangement, the seating unit is suspended from the supporting frame so as to have a semi-reclining equilibrium position when occupied, and additional rearward reclining motion is achieved by means of a mechanical drive controlled by the user, the mechanical drive including means to lock the seating unit in any desired position relative to the frame within its range of movement. This ensures that in the event of any failure of the mechanical drive, the chair should return to a position in which the user can escape from it. Additionally, by disengaging the mechanical drive when the chair is in its equilibrium position, it can then be utilized as a rocker.

Further features of the invention will become apparent from the following description of a preferred embodiment with reference to the accompanying drawings.

SHORT DESCRIPTION OF THE DRAWINGS

DESCRIPTION OF THE PREFERRED EMBODIMENT

Figure 1:
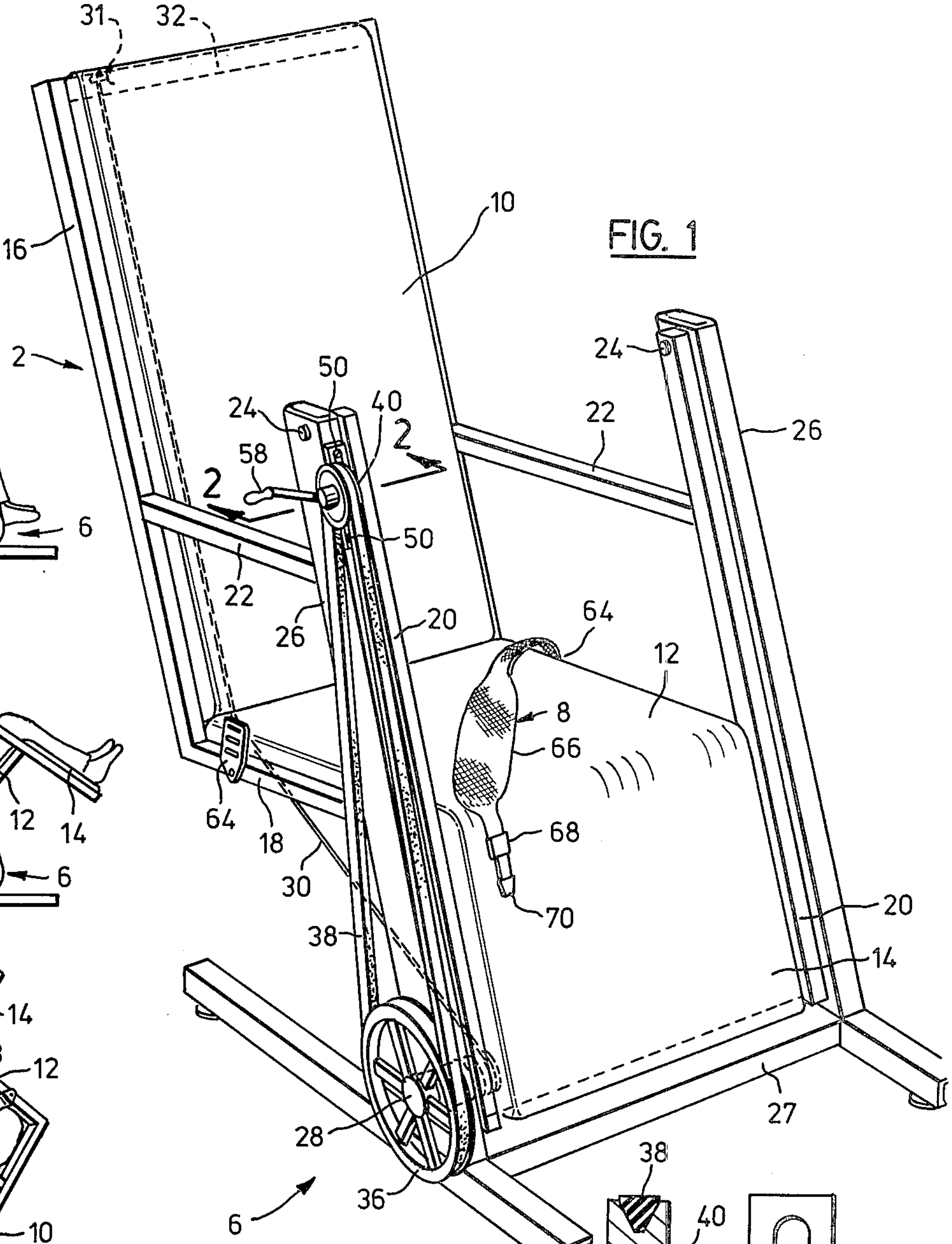
FIG. 1 is a perspective view of chair in accordance with the invention.

The principal portions of the chair of the invention comprise a seating unit indicated generally by the reference numeral 2, a supporting frame indicated generally by the reference numeral 4, a drive mechanism linking the seating unit and the frame and indicated generally by the reference numeral 6, and a restraining belt 8.

Figure 4:
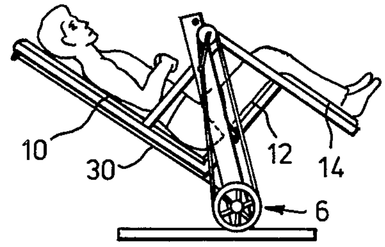

The seating unit 2 comprises a back rest portion 10, which is shown in the drawings as being straight, and which supports the head and back of a user. The back rest could also have a convex resting surface, although for reasons which will become apparent, a configuration in which the upper portion of the back rest is angled substantially forwards, as in some known chairs, will generally be undesirable. A seat portion 12 is fixed at a substantial angle to the back rest, as in conventional reclining chairs of the rester type in which the back rest and seat are formed as a unit. A further portion of the seating unit provides a rest 14 for the lower legs of a user. These portions of the seating unit are supported in a frame comprising back rest edge supports 16, seat edge supports 18, and leg rest edge supports 20. The leg rest edge supports 20 are extended upwardly and are connected to the back rest edge support by arm rests 22. The various edge supports are joined by cross members, certain of which are shown at 32 and 34, to form a rigid frame. The frame of the seating unit is suspended from the support frame 4 by means of pivots 24 which join the top ends of the edge supports 20 to inclined members 26 of the frame 4 which extend parallel to the supports 20 when the chair is upright. The upright members 26 are supported on a base 27, configured to provide stable support for the chair regardless of the position of the seating unit 6 relative to the support frame 4. The seating unit and base are configured so that, when the seating unit is occupied and assumes an equilibrium position relative to the frame suspended on the pivots 24, it is in a semi-reclining position approximately as shown in FIG. 4.

Figure 3:
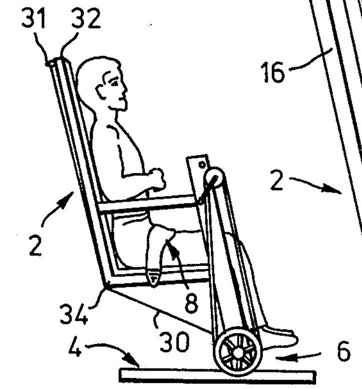
FIGS. 3, 4 and 5 illustrate the chair in upright, semi-reclining and substantially inverted positions, respectively.

Journalled in the base frame uprights 26 near their lower ends and beneath the front edge of the seat portion 12, is a horizontal shaft 28 around which is wound one end of a cable 30, the other end of which is attached to an anchorage 31 behind the cross member 32 at the top of the back rest 10. When the chair is in its upright position as shown in FIGS. 1 and 3, the cable passes down the length of the back rest from the cross member 32, around the cross member 34, and is wound onto the shaft 28. By rotation of a wheel 36 fastened to the shaft 28, the cable 30 can be wound in so as to move the chair progressively from the position shown in FIG. 3, through the position shown in FIG. 4 to the position shown in FIG. 5.

Figure 2:
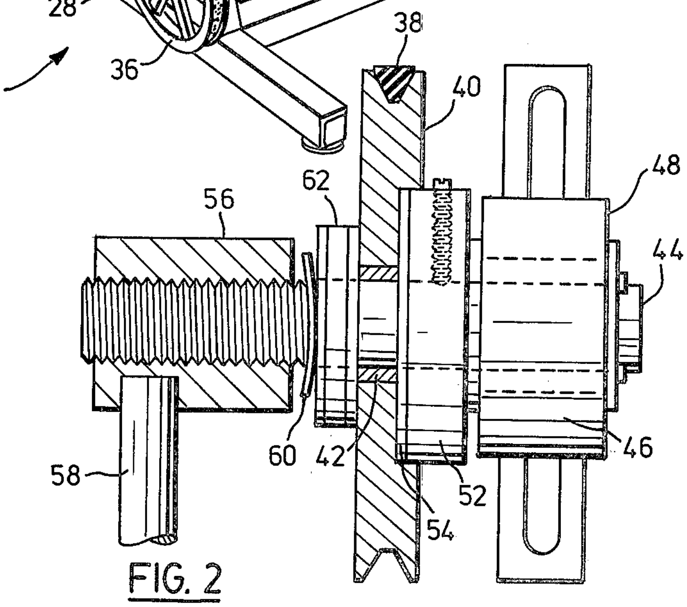
FIG. 2 is an enlarged detail, partly in section, on the line 2—2 in FIG. 1, illustrating features of the mechanical drive utilized to recline the chair.

The cable 30, the wheel 36 and the shaft 28 form part of the mechanical linkage 6 connecting the seating unit 2 to the supporting frame 4. In the embodiment shown, the pulley wheel 36 is connected by a drive belt 38 to a further pulley wheel 40 rotatably mounted on a shaft 44 by a bushing 42 (see FIG. 2). The shaft 44 is journalled in an overrunning brake unit 46 incorporated in a plummer block 48 mounted to one of the uprights 26 by bolts passing through elongated slots 52 in the plummer block, these slots allowing the position of the plummer block 48 to be moved relative to the upright 26 so as to tension the belt 38. A flange 52 is secured to the shaft 44, and a friction clutch plate 54 is sandwiched between the pulley 40 and the flange 52. The free end of the shaft 44 remote from the plummer block 48 is threaded to receive a complementarily threaded hub 56 of a crank handle 58.

When the handle 58 is wound in such a sense as to move the hub 56 on the threaded shaft 44 towards the plummer block 48, the hub 56 bears on the pulley 40 through a spring washer 60 and a thrust bearing 62 so as to force the pulley 40 towards the flange 52 and cause frictional engagement between them through the clutch plate 54. Thus the pulley 40 is locked to the shaft 44 and further movement of the handle 58 is transmitted via the pulley 40 and the belt 38 to the pulley wheel 36, thus winding the cable 30 onto the shaft 28 and reclining the chair. Reverse movement of the shaft and thus the pulley is prevented by the overrunning brake 46. When it is desired to allow the chair to return to a less reclined position, a slight movement of the handle 58 in the reverse direction will start to release the pressure on the clutch plate 54, thus releasing the effect of the overrunning brake 46 on the pulley 40 and allowing the chair to move in a controlled manner towards its equilibrium position under the influence of gravity. The chair may be returned to a fully upright position by the occupant leaning forward in the chair, and locked in that position by again moving the handle 58 in the original direction. It will of course be appreciated that a detent or detents may be provided to hold the chair in its upright or any other position.

Positioning of the axis of the handle 58 approximately in the position shown adjacent the front end of an arm rest 22 means that it is accessible to the occupant regardless of the position of the chair. It will however be understood that the mechanical arrangements for reclining the chair could be subject to considerable variation provided that any necessary controls are accessible to the occupant regardless of the position of the chair. Thus instead of a mechanical winding system, the shaft 28 could be driven by a geared electric motor under the control of switches located within reach of the occupant.

It will also be appreciated that the chair is shown in a skeleton form, and the various parts could be further covered or encased. No such covering or encasement has been shown since it forms no part of the invention and would merely obscure the operation of the working parts.

Figure 5:
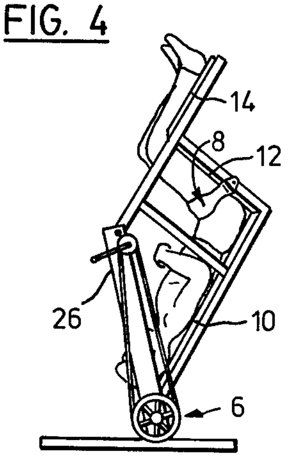

In order to restrain an occupant of the chair as it moves towards and into the position of FIG. 5, the lap belt 8 is provided. This belt operates rather differently from conventional lap safety belts, and its function is essential to the proper operation of the chair in its orthopedic mode of operation. Whilst a conventional lap safety belt passes around the pelvis of the wearer and is mainly intended to hold the pelvis of the wearer into the angle between a seat and back rest, the belt 8 of the present invention extends, when in use, between anchorages 64 on the side members 18 of the seat, and passes over the top surfaces of the thighs of the user rather than around the pelvis. In order to increase the area of engagement with the thighs, for reasons of comfort, a central portion 66 of the belt is broadened, typically to a width of about 6 inches. At least one end of the belt is releasable from its associated anchorage 64 and the belt may be provided with conventional means 68 to adjust its length. Further adjustment to obtain firm restraint of the user's thighs may be achieved by providing several alternative slots in the anchorage 64 for engagement with a hook 70 on the end of the belt.

The effect of the belt, when in position, is to hold the thigh bones of the user substantially parallel to the seat 12, without placing any direct restraint on the pelvis. The result of this arrangement is that when the chair assumes the position shown in FIG. 5, the head and torso of the user are in effect suspended from the thigh bones through the hip joints, with the pelvis destributing the load between the two thighs regardless of any inequality in the length of the legs of the user.

As will be apparent from FIG. 5, unless the torso of the user is fully vertical, some portion of the weight of the head and torso will be sustained by the head and back rest 10. If the head rest portion is angled inwardly, as is the case in some conventional reclining chairs, for example the chair of the Glass patent discussed above, this will hamper the development of tractive forces on the spine through the action of gravity. It will therefore be appreciated that such a configuration, and other features of the back rest structure which unduly restrict the development of gravitational tractive forces, should be avoided.

It will be noted that whilst in FIG. 5, the body of the user is substantially inverted, the head and torso are not in fact vertical. For the purposes of the invention, the body of the user can be considered as being substantially inverted if the chair can assume a position such that the torso of the user can reach an angle of at least 135° to its usual vertical position. A position such as that shown in FIG. 5 will usually provide adequate traction, whilst movement of the torso into a still more vertical position may render it difficult to provide adequate support for the user's lower legs without additional restraints.

Although the chair illustrated has a unitary seating unit, I do not exclude the possibility of including a reclining linkage of the lounger type in which the angle included between the seat and the back rest alters during the reclining movement, although this additional complication is not necessary for the chair to achieve its desired orthopedic function. Moreover, the foot rest 14 may be made movable relative to the remainder of the seating unit so as to provide better support for the lower legs of the user in conventional reclining positions such as shown in FIG. 4.

It will be noted that if the handle 58 is moved so as fully to release the clutch plate 54 whilst the chair is in the FIG. 4 position, it may then be used as a rocker chair, rocking about the pivots 24.

What I claim is:

1. An orthopedic reclining chair comprising a seating unit having a back rest portion and a seat portion at a substantial angle to the back rest portion, a frame supporting said seating unit for movement between a substantially upright position and a traction position in which the seat portion is maintained at a substantial angle to the back rest portion and the body of a user would be substantially inverted with the torso inclined at an angle of at least 135° to the vertical, reclining mechanism acting between said seating unit and said frame for moving the seating unit between said positions, and a lap belt extending from said seat portion and disposed to support the thighs of a user substantially parallel to said seat portion when the chair is in said traction position.

2. A chair according to claim 1, wherein the seating unit is suspended from the frame so as to assume in equilibrium a substantially semi-reclining position.

3. A chair according to claim 2, wherein the reclining mechanism is a drive mechanism manually operated by the user, and including means to lock the seating unit in any desired position relative to the frame.

4. A chair according to claim 2, wherein the reclining mechanism comprises a capstan beneath the front edge of the seat portion, and a cable extending from the capstan to the upper rear of the back rest portion.

5. A chair according to claim 4, wherein the seating unit has arm rests, and the reclining mechanism further includes a capstan drive extending from said capstan to a manually operated winding handle adjacent the front end of one arm rest.

6. A chair according to claim 5, wherein the capstan drive includes an overrunning brake releasable by reverse motion of the winding handle.

7. A chair according to claim 1, wherein the lap belt has a widened thigh-engaging portion and is located so that said widened portion will in use engage a substantial area of the front surface of the user's thighs.

* * * * *